United States Patent [19]

Harwick et al.

[11] Patent Number: 5,438,420
[45] Date of Patent: Aug. 1, 1995

[54] MONITORING OF FLUID CONTAMINATION LEVEL WHEREIN THE LIGHT ENERGY IS FOCUSED ON THE FLUID PASSAGE MEANS

[75] Inventors: Warren J. Harwick, Rochester, Mich.; Holger T. Sommer, Merlin; Kenneth L. Girvin, Grants Pass, both of Oreg.

[73] Assignees: Vickers, Incorporated, Maumee, Ohio; Met One, Inc., Grants Pass, Oreg.

[21] Appl. No.: 103,352

[22] Filed: Aug. 9, 1993

[51] Int. Cl.⁶ .......................................... G01N 21/00
[52] U.S. Cl. .................................. 356/440; 356/442
[58] Field of Search ............... 356/436, 440, 441, 442; 250/573, 574, 575

[56] References Cited

U.S. PATENT DOCUMENTS

| | | | |
|---|---|---|---|
| 3,141,094 | 7/1964 | Strickler | 356/440 |
| 3,740,155 | 6/1973 | Keller et al. | 356/246 |
| 3,784,307 | 1/1974 | Jackson et al. | 356/436 |
| 3,794,428 | 2/1974 | Giesecke | 356/440 |
| 4,181,009 | 1/1980 | Williamson | |
| 4,561,779 | 12/1985 | Nagamune et al. | 356/440 |
| 4,797,000 | 1/1989 | Curtis | 356/436 |
| 4,917,496 | 4/1990 | Sommer | |
| 4,979,822 | 12/1990 | Sommer | |
| 5,033,851 | 7/1991 | Sommer | |
| 5,049,742 | 9/1991 | Hosonuma et al. | |
| 5,077,481 | 12/1991 | Hoult | |
| 5,173,742 | 12/1992 | Young | 356/440 |

FOREIGN PATENT DOCUMENTS

| | | |
|---|---|---|
| 0448089A2 | 9/1991 | European Pat. Off. |
| 1557465 | 12/1979 | United Kingdom |
| WO91/08467 | 6/1991 | WIPO |
| 9306458A2 | 4/1993 | WIPO |

OTHER PUBLICATIONS

Vickers, Incorporated, "Vickers Guide to Systematic Contamination Control", 1992.

Primary Examiner—Richard A. Rosenberger
Assistant Examiner—Robert Kim
Attorney, Agent, or Firm—Barnes, Kisselle, Raisch, Choate, Whittemore & Hulbert

[57] ABSTRACT

Apparatus for monitoring fluid contaminant level that includes a light source positioned on one side of a fluid sample path for directing light energy into fluid flowing in the sample path, a photosensor positioned on the same side of the sample path, and a reflector positioned on an opposing side of the sample path for receiving light from the source transmitted through the sample fluid and reflecting such light back through the fluid to the photosensor. The photosensor provides an electrical signal as a function of intensity of light incident thereon from the light source after having twice passed through the fluid, and the concentration or level of contaminants in the fluid is indicated as a function of such electrical signal. Thus, the concentration of contaminants that extinguish light energy transmitted through the fluid is indicated as an inverse function of light intensity at the photosensor, and may be compared to a preset target threshold level for indicating an undesirably high contamination level.

5 Claims, 2 Drawing Sheets

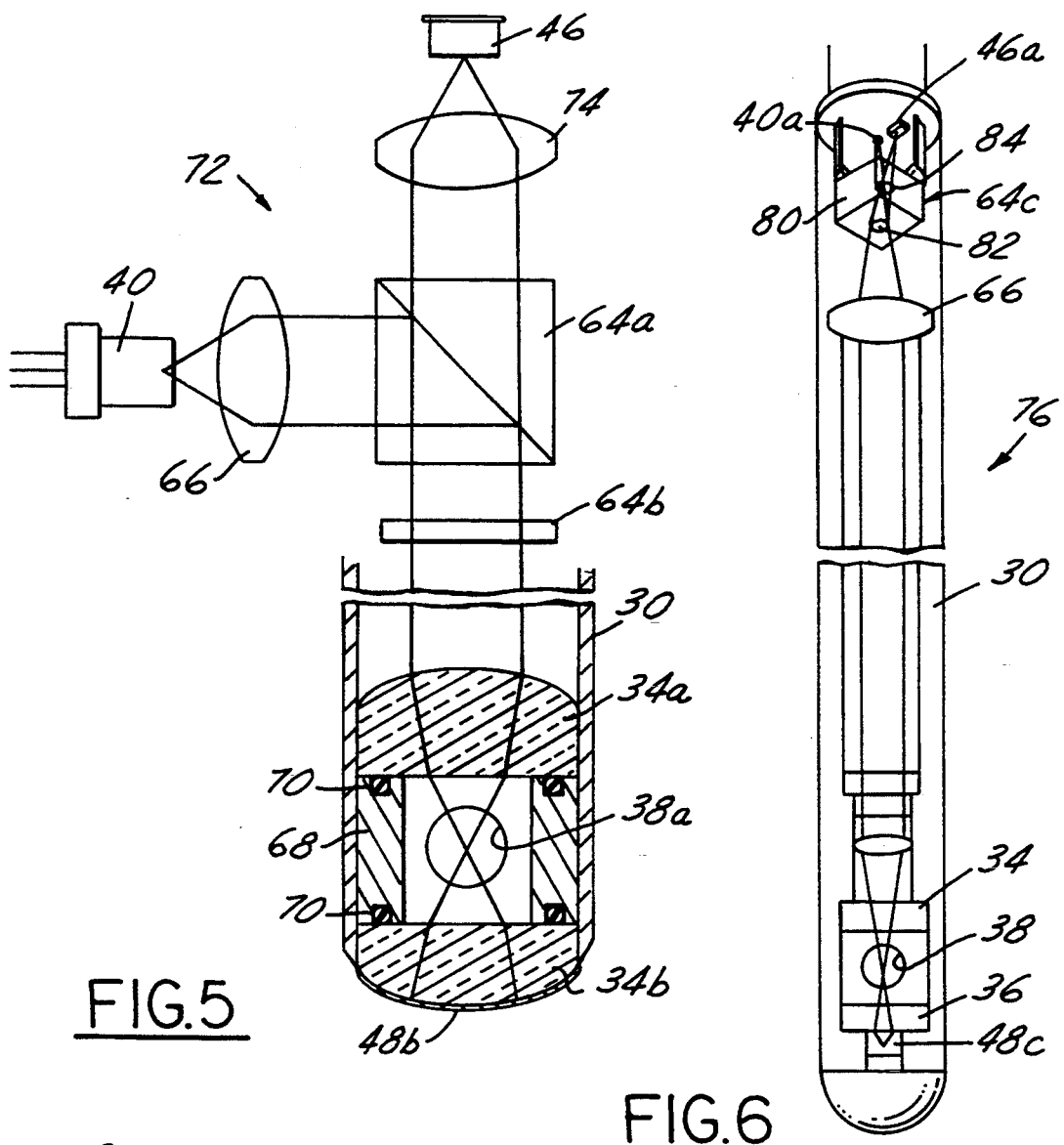
FIG. 5
FIG. 6
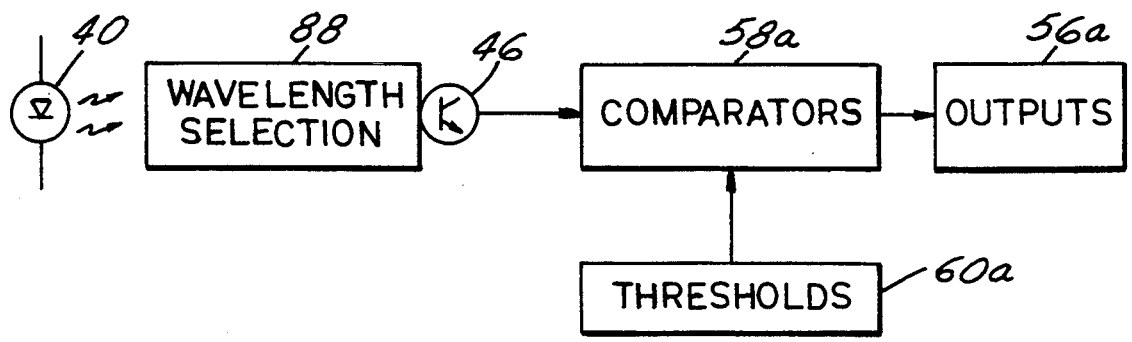
FIG. 7

MONITORING OF FLUID CONTAMINATION LEVEL WHEREIN THE LIGHT ENERGY IS FOCUSED ON THE FLUID PASSAGE MEANS

The present invention is directed to systemic contamination control of fluids, and more particularly to a method and apparatus for continuous in-line monitoring of fluid contamination level in hydraulic and lubrication systems.

BACKGROUND AND OBJECTS OF THE INVENTION

It has heretofore been recognized in design and operation of hydraulic and lubrication systems that control of contaminant concentration level in the circulating fluid plays an important role in system reliability. Solid particulate contaminants, such as sand, dirt and metal particles, may enter the system at the time of manufacture or upon breach of system integrity, or may result from abrasion and wear of system components. Air bubbles and water droplets may become entrained in the fluid for any number of reasons, and can cause damage and corrosion of system components. Proper selection and placement of contamination control devices can eliminate the root cause of up to 80% of system failures. In addition, proper identification of target cleanliness levels, coupled with proper selection and placement of suitable filters or other contamination control devices, allows the cost of the filters and devices to be recovered quickly by the savings of improved performance, increased component life, increased oil life, increased system up-time and reduced repairs.

In systemic contamination control, the goal is to maintain fluid cleanliness at or below the point at which contamination can be become a factor in the failure of any component in the system during the desired useful life of that system. The first step in achieving this goal is identifying and setting a target cleanliness level at the system design stage that takes into account the specific needs and components of the system. These target contamination levels are determined by component design and system operating characteristics. For example, target cleanliness level would typically be greater (lower number), and therefore allowable contamination concentration level would typically be less, for systems operating at high fluid pressure than for systems operating at low pressure. The next step is to select and position filters and other contamination control devices so that the target cleanliness level can be maintained in a cost-effective manner. The third step is to confirm that the desired target cleanliness level is being maintained. For a detailed discussion of systemic contamination control, see the "Vickers Guide to Systemic Contamination Control." Vickers, Incorporated, December 1992. The present invention is directed in particular to the third or fluid-monitoring step in the systemic approach to fluid contamination control.

Fluid cleanliness level is typically monitored by obtaining a fluid sample from the system during operation, and transmitting the sample to a laboratory that analyzes and reports cleanliness level in the form of cleanliness data in an established standard data format—e.g., ISO Standard 4406. If the target cleanliness level is being met, standard filter maintenance and periodic fluid testing are continued. If the target cleanliness level is not being maintained, a change in maintenance practices and perhaps addition or relocation of the filters, may be warranted. This conventional technique for monitoring contamination level requires several hours or days to obtain the laboratory test results, and therefore leaves much to be desired in terms of providing an accurate indication of contamination level in real time so that corrective action can be initiated before the problem becomes more serious.

It is therefore a general object of the present invention to provide a system and method for proactive maintenance of fluid cleanliness in hydraulic, lubrication and other fluid systems in which one or more sensors are placed in the fluid flow path for monitoring fluid cleanliness and providing a continuous indication of fluid cleanliness level in real time. Another and more specific object of the present invention is to provide a method and apparatus for monitoring fluid contamination level that embody no consumable parts, that possess enhanced flexibility in terms of placement in the system, that do not substantially restrict fluid flow, that are responsive to all three of the primary types of contaminants (solid particles, water droplets and air bubbles), that provide continuous and unattended monitoring in real time, that are readily programmable in the field for detecting differing target cleanliness levels, that have a sensitivity of plus or minus one ISO code, and/or that warn a user of changes in contaminant concentration level before the system pump and other fluid components are adversely affected. Another and more specific object of the present invention is to provide a fluid contamination level monitoring apparatus of the described character that is economical to manufacture, and that may be readily installed in either new or existing industrial or mobile fluid systems.

SUMMARY OF THE INVENTION

Apparatus for monitoring fluid contaminant level in accordance with the present invention includes a light source positioned on one side of a fluid sample path for directing light energy into fluid flowing in the sample path, a photosensor positioned on the same side of the sample path, and a reflector positioned on the opposing side of the sample path for receiving light from the source transmitted through the sample fluid and reflecting such light back through the fluid to the photosensor. The photosensor provides an electrical signal as a function of intensity of light incident thereon from the light source after having twice passed through the fluid, and the concentration or level of contaminants in the fluid is indicated as a function of such electrical signal. Thus, the concentration of contaminants that extinguish (scatter, absorb or otherwise block) transmission of light energy through the fluid is indicated as an inverse function of light intensity at the photosensor, and may be compared to a preset target threshold level for indicating an undesirably high contamination level—i.e., approaching or exceeding the design target contamination level.

In a fluid system that includes a pump, a fluid reservoir and plumbing for circulating fluid in a closed path from the reservoir through the pump and various system components back to the reservoir, the monitoring apparatus of the present invention preferably takes the form of a housing that contains the light source, photosensor and suitable control electronics, and an elongated hollow probe that extends from the housing into the reservoir upstream of the pump inlet. A pair of optical windows are positioned within the hollow probe remotely of the housing, and openings in the probe sidewall admit fluid to the area between the windows. The reflector is positioned in the probe on the opposing side of the windows, and may take the form of a reflective coating on the exterior surface of the window remote from the light source and photosensor, or a separate retroreflector positioned adjacent to such remote window. The windows may comprise plano-convex lenses for focusing the light energy to a point within the sample fluid path during transmission in both directions through the sample fluid. Light energy may be transmitted through the probe to and from the light source and photosensor by respective optical fibers, or may be transmitted along a common optical path and separated by a beam splitter at the light source and photosensor. In various embodiments of the invention, the beam splitter takes the form of a polarized beam splitter and a quarter-wave plate for rotating polarization of the light energy and thereby separating energy from the light source from that incident on the photodetector, or a holographic optical pick-up with a hologram and grating for separating the transmitted and return light energies.

The light source preferably comprises a laser diode that transmits light energy in the near-infrared wavelength range, which has the advantage of rendering the optics substantially immune from ambient light, and also substantially immune from changes in fluid color as the fluid ages. In the preferred embodiments, light at all wavelengths transmitted by the laser diode is collected and effectively integrated at the photosensor, so that the photosensor is simultaneously responsive to all types of contaminants without distinguishing among contaminants. Alternatively, the return light energy may be separated as a function of wavelength prior to incidence on the photosensor for sensing different types of contaminants. The apparatus and method of the present invention find particular utility in conjunction with hydraulic and lubrication fluid systems, but may also be employed in conjunction with water/glycol and phosphate ester fluid circulation systems.

BRIEF DESCRIPTION OF THE DRAWINGS

The invention, together with additional objects, features and advantages thereof, will be best understood from the following description, the appended claims and the accompanying drawings in which:

FIGS. 4-7 are schematic diagrams of respective modified embodiments of the monitor illustrated in FIG. 2; and FIG. 7 is a functional block diagram of a modification to the contamination monitor as illustrated in FIG. 3.

DETAILED DESCRIPTION OF PREFERRED EMBODIMENTS

The disclosure of the "Vickers Guide to Systemic Contamination Control," Vickers, Incorporated, December 1992 is incorporated herein by reference for purposes of background.

Figure 1:
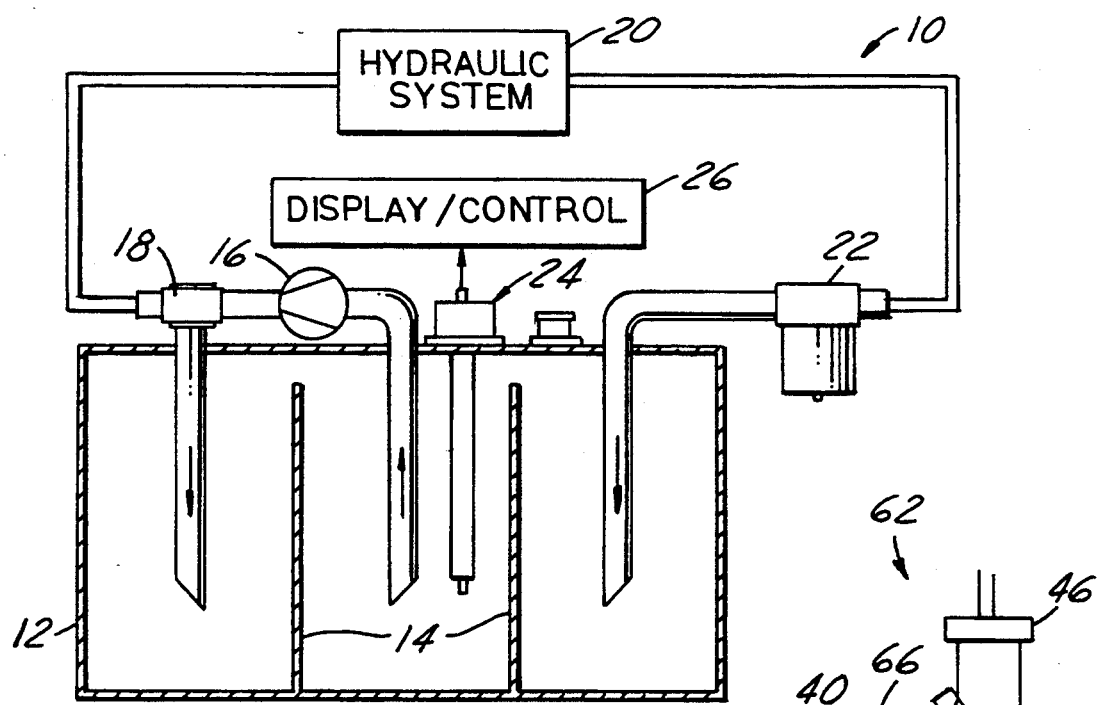
FIG. 1 is a schematic diagram of a hydraulic fluid power system that includes a contamination monitor in accordance with a presently preferred embodiment of the invention.

FIG. 1 illustrates a hydraulic fluid power system 10 as comprising a fluid reservoir 12 having sections separated by baffles 14. A pump 16 draws fluid from the center section of reservoir 12, and feeds such fluid under pressure through a relief valve 18 to the various components of hydraulic system 20. Fluid is returned from system 20 to one end section of reservoir 12 through a filter 22. Relief valve 18 returns fluid to the other end section of reservoir 12. To the extent thus far described, system 10 is of conventional construction. A contamination monitor 24 in accordance with the present invention is mounted on reservoir 12 so as to extend into the fluid within the reservoir adjacent to the inlet of pump 16, and is connected to appropriate electronics 26 for displaying contamination level and/or controlling system components in the event that contamination level becomes excessive.

Figure 2:
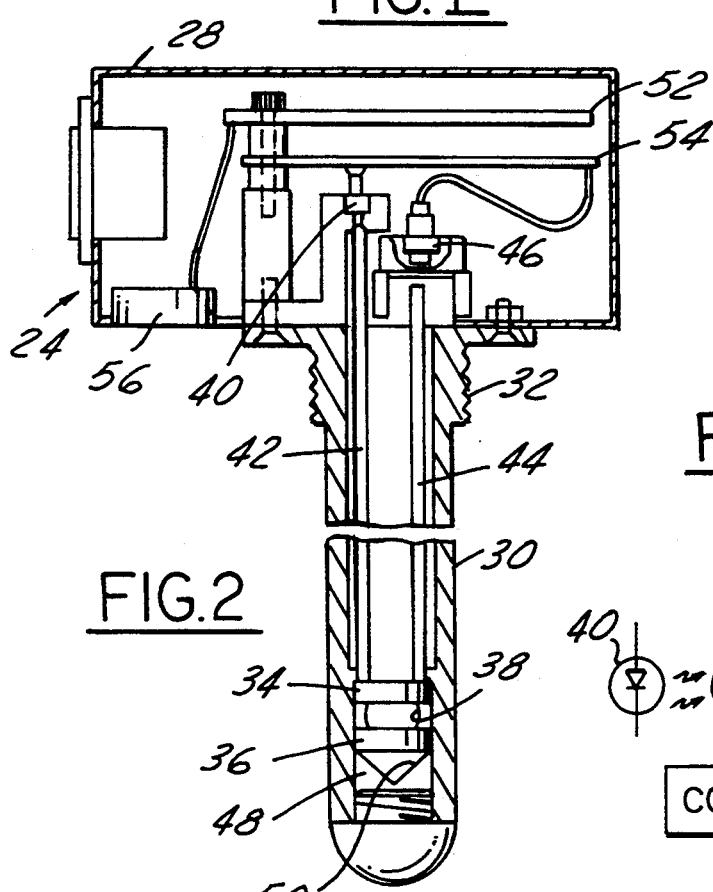
FIG. 2 is a fragmentary sectional view of the contamination monitor in the system of FIG. 1.
Figure 3:
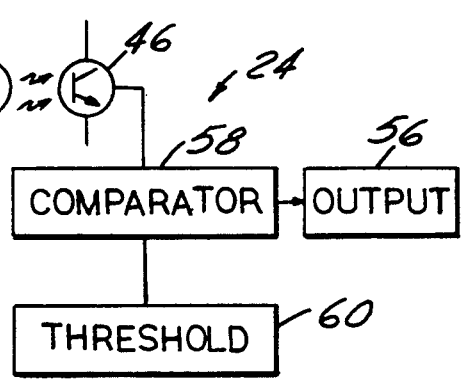
FIG. 3 is a functional block diagram of the contamination monitor illustrated in FIG. 2.

FIG. 2 illustrates contamination monitor 24 in greater detail as comprising a closed housing 28 having an elongated hollow probe 30 affixed to and projecting from one housing sidewall. Probe 30 has external threads 32 adjacent to housing 28 for mounting the monitor assembly in an internally threaded gland (not shown) on the top of reservoir 12 (FIG. 1). A pair of optically transparent windows 34,36 are mounted within probe 30 remotely of housing 28, and are spaced from each other for admitting fluid therebetween through diametrically opposed openings 38 in the sidewall of probe 30. A laser diode 40 is mounted within housing 28 and aligned with a optical fiber 42 that transmits light from diode 40 to window 34 longitudinally through the interior of probe 30. A second optical fiber 44 extends through the interior of probe 30 for transmitting light from window 34 to a photosensor 46 within housing 28. A retroreflector 48 is positioned adjacent to window 36 at the housing-remote end of probe 30, and has a reflective surface 50 aligned with the ends of fibers 42,44 at window 34. A pair of circuitboards 52,54 are mounted within housing 28, and are electrically connected to diode 40 and photosensor 46. Circuitboards 52,54 include electrical circuitry (FIG. 3) responsive to light energy at photosensor 46 for determining fluid contaminant level, and for providing corresponding output signals to a terminal strip 56 on the exterior of housing 28 for connection to display/control electronics 26 (FIG. 1).

In operation, fluid continuously flows through probe openings 38 between windows 34,36. Light energy is transmitted from diode 40 through optical fiber 42 to window 34, where the light energy emerges as a collimated beam that is transmitted through window 34, through the fluid between windows 34,36 and through window 36 onto reflector 40. Such light energy is reflected from surface 50 of reflector 48 back through window 36, through the fluid between windows 34,36 and through window 34 to fiber 44. Such reflected light energy is carried by fiber 44 to photosensor 46, which provides an electrical signal indicative of intensity of light incident on the photosensor. Thus, only light energy transmitted directly through the fluid in both directions is incident on photosensor 46, which is to say that any light energy extinguished (i.e.—absorbed, scattered or otherwise blocked) by the fluid, or contaminants contained in the fluid, does not reach the photosensor. By traversing the test fluid sample twice between diode 40 and photosensor 46, sensitivity of apparatus 24 is effectively doubled.

The intensity of light incident on photosensor 46, and consequently the electrical signal generated by photosensor 46, is an inverse function of the concentration of solid particulate, air bubble and water droplet contaminant concentration within the fluid between windows 34,36, and thus provides a direct indication of contaminate concentration level. That is, as concentration of any one or more of these three types of contaminants increase in the fluid, the amount of light extinguished by such contaminants will increase, and consequently the amount of light twice transmitted through the sample and incident on photosensor 46 will decrease. On the other hand, since the volume of fluid between windows 34,36 remains constant, the amount of light absorbed by the fluid itself remains substantially constant. In this respect, it will be appreciated that the use of light in the near-infrared range not only renders the system substantially immune to stray ambient light, but also immune to normal color changes that will occur in the fluid itself as it ages. The electrical output of photosensor 46 is fed to a comparator circuit 58 (FIG. 3) where such electrical signal is compared to a preset threshold 60 indicative of the desired target contaminant level. When the contaminant level increases beyond such target level, comparator 58 provides a corresponding signal to output terminal block 56, and thence to the display and/or control circuitry 26 (FIG. 1) connected to such terminal block.

Monitor 24 is calibrated by directing a test fluid between windows 34,36 of known contamination level, preferably equal to the target contamination level of the system in question. The test fluid may contain different types of contaminants, or a "standard contaminant" at a concentration empirically found to correspond to the desired target contaminant level. Threshold circuit 60 is then adjusted until comparator 58 just indicates target contaminant level at output 56. Thereafter, during operation, such output will be provided whenever gross contaminant level reaches this target level. Of course, further analysis of fluid contaminants may be needed to determine contaminant size, type and source.

Figure 4:
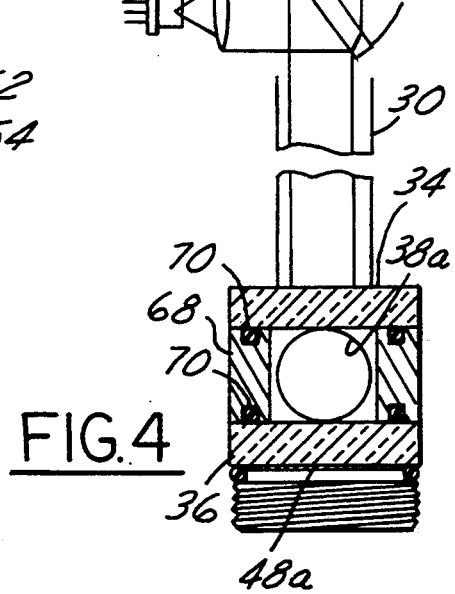

FIGS. 4-7 illustrate modified contamination monitors in accordance with the present invention. In these figures, reference numerals identical to those employed in FIGS. 2-3 or in each other indicate identical elements, and reference numerals with a letter suffix indicate modified elements. In FIG. 4, a modified contamination monitor 62 includes a beam splitter 64 for reflecting light energy from diode 40 collimated by a lens 66 through probe 30 to window 34, and transmitting return light energy onto photosensor 46. Windows 34,36 are spaced from each other by a collar 68 having sealing rings 70 that engage the respective windows. Openings 38a are formed at diametrically opposed sides of collar 68 for admitting fluid between windows 34,36. The retroreflector in this embodiment takes the form of a reflective coating 48a on the exterior surface of window 36. Thus, light energy from diode 40 is collimated by lens 66, reflected by beam splitter 64 through the hollow interior of probe 30, through window 34, through fluid between windows 34,36 and through window 36 onto reflective layer 48a. Such light energy is reflected back through window 36, the fluid between windows 34,36, through window 34, through the hollow interior of probe 30 and through beam splitter 64 onto photosensor 46.

The monitor 72 in FIG. 5 includes a polarized beam splitter 64a, and a quarter-wave plate 64b disposed between beam splitter 64a and the hollow interior of probe 30. Thus, the polarization of light energy from diode 40 is rotated 90° during each passage through quarter-wave plate 64b, so that polarized beam splitter 64a functions to separate the transmitted and return light energy. The return energy is transmitted to photosensor 46 through a focusing lens 74. The windows 34a and 34b in the embodiment of FIG. 5 take the form of plano-convex lenses, with window 34b again having the retroreflector formed as a coating 48b on the exterior surface thereof. Thus, the incident and return light energy is focused by lens/windows 34a,34b to a point within the sample space between the windows.

In the monitor 76 of FIG. 6, a laser diode 40a and a photosensor 46a are combined in a holographic optical pick-up beam splitter 64c. A holographic element 80 within pick-up 78 has a hologram 82 and a grating 84, which together function in the usual manner for splitting or separating the energy radiated by diode 40 from the return energy focused onto photosensor 46.

As noted above, all of the return energy is focused onto photosensor 46 in the embodiments of FIGS. 2-6, so that the photosensor is responsive to return energy at all of the near-infrared wavelengths radiated by the diode, and does not distinguish between different types of contaminants. In the modified electronics 86 illustrated in FIG. 7, a wavelength selection mechanism 88, such as a rotatable or tiltable filter element, is positioned adjacent to photosensor 46 for selecting one or more specific wave bands of return light incident on the photosensor. In this way, the photosensor is selectively sensitive to specific types of contaminants that absorb energy at specific wavelengths. Multiple comparators 58a are synchronized with operation of wavelength selection mechanism 88 for comparing return energy at each of the selected wavelengths or wave bands with an associated threshold 60a, and providing corresponding signals to output terminal block 56a when specific contaminants exceed the desired threshold or target levels.

We claim:

1. Apparatus for monitoring fluid contaminant level comprising:
    an elongated probe,
    first means adjacent to one end of said probe providing a passage for sample fluid flow through said probe in a direction orthogonal to said probe,
    a light source at a second end of said probe for directing collimated light energy along a light path within said probe toward said fluid passage,
    retroreflective means disposed at said one end of said probe on a side of said fluid passage opposite said light source,
    second means disposed within said probe between said light source and said fluid passage for cooperating with said retroreflective means to focus collimated light energy from said source to a point in said fluid passage and thence onto said retroreflective means, said retroreflective means reflecting and refocusing said light energy to the same said point in said fluid passage and thence onto second means for recollimazation and passage back along the same second light path in said probe toward said light source,
    third means in said light path between said light source and said second means for separation from said path the light energy reflected for said retroreflective means, and
    photosensing means at said second end of said probe for receiving light energy separated from said light path by said third means and providing an indication of level of contamination in the fluid in said passage as a function of intensity of such light energy.

2. The apparatus set forth in claim 1 wherein said third means comprises a hologram and a grating disposed in series in said light path.

3. The apparatus set forth in claim 1 wherein said third means comprises a polarized beam splitter and a quarter-wave plate disposed in series in said light path.

4. The apparatus set forth in claims 1, 2 or 3 wherein said second means comprises a pair of plano-convex lenses disposed on opposed sides of said fluid passage and having a common focus within said passage.

5. The apparatus set forth in claim 4 wherein said retroreflective means comprises a reflective coating on a surface of the said plano-convex lens remote from said light source.

* * * * *

UNITED STATES PATENT AND TRADEMARK OFFICE
CERTIFICATE OF CORRECTION

PATENT NO. : 5,438,420
DATED : August 1, 1995
INVENTOR(S) : Warren J. Harwick, Holger T. Sommer and Kenneth L. Girvin It is certified that error appears in the above-indentified patent and that said Letters Patent is hereby corrected as shown below:

Claim 1, column 6, line 59, delete "second" and replace with --said--.

Signed and Sealed this

Twenty-fifth Day of February, 1997

Attest:

BRUCE LEHMAN

*Attesting Officer*   *Commissioner of Patents and Trademarks*